United States Patent [19]

Leschek

[11] 4,039,767
[45] Aug. 2, 1977

[54] ACOUSTIC EMISSION TRANSDUCER CALIBRATION

[75] Inventor: Walter C. Leschek, Pittsburgh, Pa.

[73] Assignee: Westinghouse Electric Corporation, Pittsburgh, Pa.

[21] Appl. No.: 595,982

[22] Filed: July 14, 1975

[51] Int. Cl.² .............................................. H04R 29/00
[52] U.S. Cl. ............................... 179/175.1 A; 181/140
[58] Field of Search .................. 179/175.1 A; 324/56; 181/139, 140

[56] References Cited

FOREIGN PATENT DOCUMENTS 1,066,622  10/1959  Germany ....................... 179/175.1 A

OTHER PUBLICATIONS

Researches of the Electrotechnical Laboratory, No. 706, Jan. 1970, "Reciprocity Calibration . . . In a Diffuse Sound Field" by Nakajima, 179-175.1A.
RCA Review; vol. VI, No. 1, July 1941, "Calibration of Microphones, by . . . Reciprocity" by Olson, 179-175-.1A.

Primary Examiner—David L. Stewart
Attorney, Agent, or Firm—Z. L. Dermer; M. S. Yatsko

[57] ABSTRACT

A method of calibrating acoustic emission transducers. The sensitivity of a standard transducer is first determined utilizing a reciprocity calibration technique, and the standard transducer and the acoustic emission transducer are then connected to a bounded acoustic medium. Random acoustic white noise is transmitted into the acoustic medium thereby establishing a multi-mode reverberant sound field, and the output responses from the standard transducer and the acoustic emission transducer to the reverberant sound field are obtained and compared to determine the sensitivity of the acoustic emission transducer.

7 Claims, 4 Drawing Figures

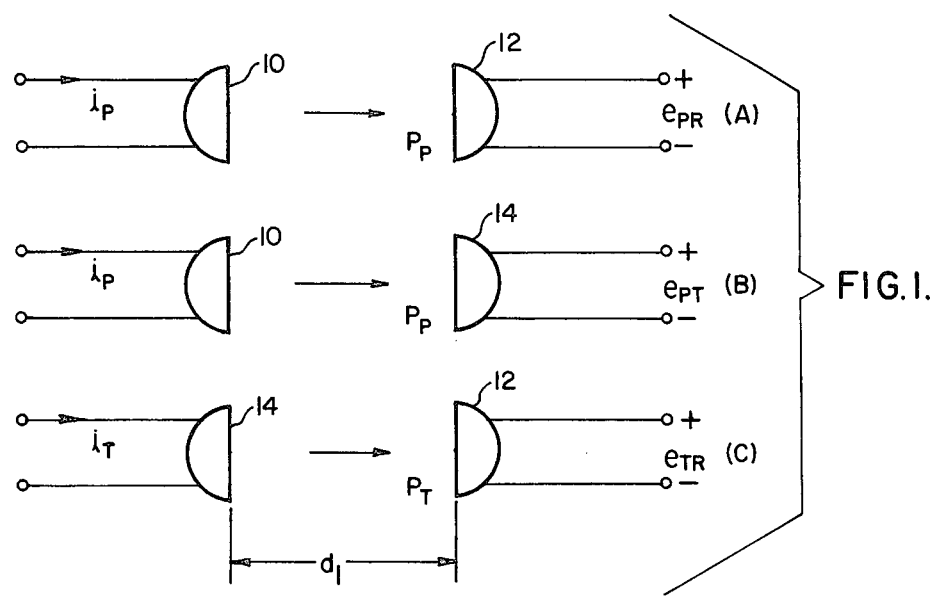
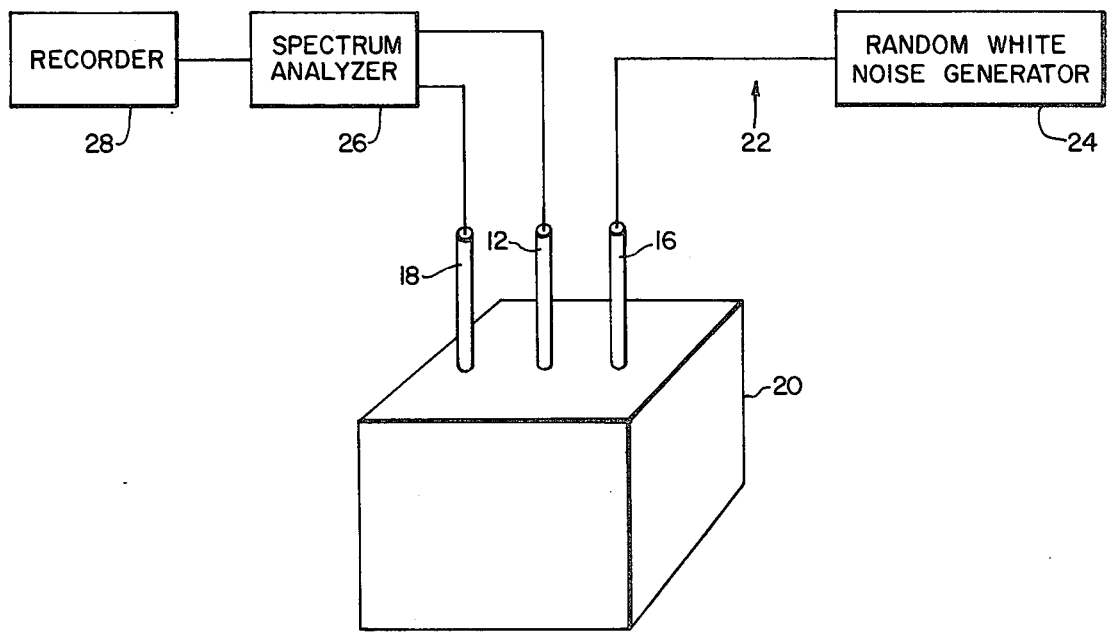

ACOUSTIC EMISSION TRANSDUCER CALIBRATION

BACKGROUND OF THE INVENTION

This invention relates generally to transducers, and more particularly to a method of calibrating acoustic emission transducers.

The use of electroacoustic sensor elements as flaw detectors for metal vessels is widespread. In its simplest form, a piezoelectric element is acoustically coupled to the medium which is to be monitored, and the electrical signal derived therefrom indicates the condition of the medium under study. Acoustic emission transducers have been proposed for use as passive listening devices to detect the noise being emitted by growing flaws as, for example, in monitoring the metal wall of a nuclear reactor pressure vessel. Such electroacoustic transducers are affixed to the exterior pressure vessel wall, and remain in place for monitoring of the vessel wall condition during operation. However, in order to be useful for nuclear reactor service, the sensitivity of the acoustic emission transducer at the various monitoring frequencies must be determined when acoustically loaded by a medium representative of a nuclear reactor pressure vessel. Without such calibration, meaningful data would not be supplied by the acoustic emission transducer.

One method used to calibrate acoustic emission transducers consists of coupling the face of the acoustic emission transducer directly against the face of a transmitting transducer having a flat transmitting response, and electrically driving the transmitting transducer in the fashion of a loudspeaker. The receiving response of the acoustic emission transducer is then measured. However, when applied to transducers intended for nuclear reactor use, this technique gives results that are in disagreement with those obtained during field tests. The disagreement in results is caused by the transducers not being loaded by a representative acoustic medium during calibration.

Another method utilized to calibrate acoustic emission transducers is to mount the transducers on a long, thin bar, and to excite the bar with spark-generated simulated acoustic emission pulses. While the impulsive nature of the spark-generated sound is closer to that generated in the nuclear reactor than with the first method, this second method also is prone to the same problem as is the first method; namely, the acoustic loading is unrepresentative of the actual loading which will be experienced during use.

SUMMARY OF THE INVENTION

The aforementioned problem of prior art is eliminated by this invention by providing a means for calibrating the sensitivity of an acoustic emission transducer. The sensitivity of a primary standard transducer is first determined at selected frequencies over a predetermined range of frequencies. The standard transducer and the acoustic emission transducer are then placed in acoustical communication with a bounded acoustic medium representative of the medium on which the acoustic emission transducer will be used. Random acoustic white noise is transmitted into the acoustical medium thereby establishing a multimode reverberant sound field, and the output response of both the standard transducer and the acoustic emission transducer are measured at selected frequencies within the predetermined range of frequencies. The output response of the acoustic emission transducer is then compared with the output response of the standard transducer to determine the sensitivity of the acoustic emission transducer.

BRIEF DESCRIPTION OF THE DRAWINGS

Reference is now made to the description of the preferred embodiment, illustrated in the accompanying drawings, in which:

FIG. 1 schematically illustrates the reciprocity method of determining the receiving sensitivity of the standard transducer;

FIG. 2 diagrammatically illustrates the location of the transducers during calibration;

DESCRIPTION OF THE PREFERRED EMBODIMENT

Figure 3:
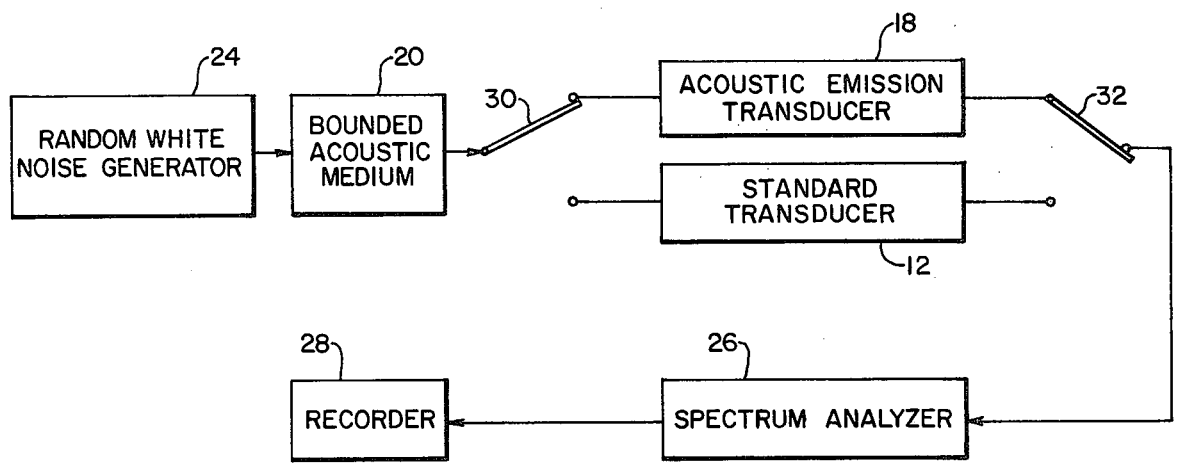
FIG. 3 schematically illustrates the signal transmission path associated with this invention.

The acoustic emission transducer is calibrated by comparing its output signals against that of a primary standard transducer. As such, the primary standard transducer must be calibrated before the acoustic emission transducer can be calibrated. The primary standard transducer should be calibrated independently, using a technique which will accurately determine the sensitivity of the standard transducer. One such calibration technique, commonly used for calibrating electroacoustic standards for use in air and in liquids, is the reciprocity calibration technique. The primary advantage of reciprocity calibration is that it avoids the necessity of attempting to produce measurable or calculatable sound pressures, since all the basic measurements, other than the distance between transducers, and the density of the acoustic medium are electrical in nature.

The conventional reciprocity calibration procedure (See FIG. 1) requires the use of three transducers 10, 12, 14: one 10 serves only as a projector; one 12 is a reciprocal transducer and serves as both a projector and receiver; one 14 serves only as a receiver. To be reciprocal, a transducer must be linear, passive, and bilateral. For a reciprocal transducer 12, the equation $$M/S = J = 2d/\rho f$$

is valid: where $M$ is the free-field voltage sensitivity, $S$ is the transmitting current response, $J$ is the reciprocity parameter, $d$ is the distance between transducers, $\rho$ is the density of the acoustic medium, and $f$ is the frequency at which the calibration is made.

The free-field voltage sensitivity, M, of an electroacoustic transducer used for sound reception is defined as the ratio of the output open-circuit voltage to the free-field sound pressure in the undisturbed plane progressive wave. The frequency and angle of incidence must be specified. The transmitting current response, S, of an electracoustic transducer for sound emission is defined as the ratio of the sound pressure that appears at a distance of 1 meter in a specified direction from the effective center of the transducer due to the signal current flowing into the electrical input terminals.

Three measurements are needed for a conventional reciprocity calibration. In the first measurement, FIG. 1a, the projector 10 is driven with a constant current $i_P$ and the open-circuit voltage $e_{PR}$ of the receiver 12 is measured. The driving current $i_P$ and open-circuit receiving voltage $e_{PR}$ are related through the equation $$e_{PR} = M_R P_P = M_R (i_P S_P d_O/d_1) \qquad (1)$$

Here $d_O$ is the reference distance at which the transmitting current response of the projector, $S_P$, is specified and $d_1$ is the actual separation distance between transducers.

In the second measurement, FIG. 1b, the projector 10 is again driven with a constant current, $i_p$ and the open-circuit voltage $e_{PT}$ of the reciprocal transducer 14, is measured. The current, $i_P$, and the voltage, $e_{PT}$, are related through the equation $$e_{PT} = M_T P_P = M_T (i_P S_P d_O/d_1) \qquad (2)$$

Combining Eq. (1) and Eq. (2) yields the relationship $$M_R = M_T(e_{PR}/e_{PT}) \qquad (3)$$

Since transducer 14 is reciprocal, that is, $M_T = J_O S_T$, Eq. (3) can be rewritten as $$M_R = S_T J_O (e_{PR}/e_{PT}) \qquad (4)$$

where $$J_O = 2d_O/\rho f$$

In the third measurement, FIG. 1c, the reciprocal transducer, 14, is driven with a current $i_T$ and the open-circuit voltage $e_{TR}$ of the receiver, 12, is measured, yielding $$e_{TR} = M_R P_T = M_R(i_T S_T d_O/d_1) \qquad (5)$$

or $$M_R = (e_{TR}/i_T S_T)(d_1/d_O) \qquad (6)$$

Multiplying Eq. (4) and Eq. (6) together yields $$M_R^2 = J_1 (e_{PR} e_{TR}/e_{PT} i_T)$$

or $$M_R = [J_1(e_{PR} e_{TR}/e_{PT} i_T)]^{1/2} \qquad (7)$$

where $$J_1 = 2d_1/\rho f$$

$M_R$ is the free-field voltage sensitivity of the primary standard transducer 12.

A primary standard transducer 12 should be chosen which has a flat receiving versus frequency response. This response should be unaffected by the acoustic loading of the operating medium. Although this is not a fundamental requirement, it does simplify the comparison calibration of the acoustic emission transducer. The sensitivity of the standard transducer 112 should also be stable with time. A transducer having the aforementioned characteristics which may be utilized is one using lithium sulfate as the natural piezoelectric crystal. This standard transducer is well known in the nondestructive testing art, and is commercially available therein.

The driving currents, $i$, are alternating current sine waves, and are varied over the range of frequencies for which it is desired to calibrate the acoustic emission transducer. For use in nuclear reactor installations, a range which has been found satisfactory for monitoring purposes is from approximately 100 kHz to approximately 1.1 MHz. The measurement of the receiving sensitivity of the standard transducer 12 would occur at selected frequencies within this larger range of frequencies. For examples, the current, $i$, would be varied over the range of frequencies in increments of 10 kHz. As heretofore mentioned, the sensitivity, $M_R$, of the standard transducer 12 should be substantially constant over the entire range of frequencies. During the calibration, the sine wave is gated, by means not shown, to eliminate unwanted signals arriving by reflected paths.

Referring more particularly to FIG. 2, once the sensitivity of the primary transducer 12 has been determined over the desired range of frequencies, the standard transducer 12 and the acoustic emission transducer 18 for which calibration is desired are placed in acoustical communication with a bounded acoustic medium 20 presenting a substantially equivalent acoustic loading to the medium on which the acoustic emission transducer 18 is to be used, acoustic loading being the acoustic impedance presented by the medium. The standard transducer 12 and the acoustic emission transducer 18, for example, are secured to a solid steel block 20 having each of its three dimensions at least comparable to the approximate thickness of the nuclear reactor pressure vessel wall, the intended monitored medium.

In addition to being similar in dimension to the wall thickness of a nuclear reactor pressure vessel, the acoustic medium 20 is constructed to have mechanical resonances which will not obscure the measured frequency response of the transducer 18. The acoustic medium, or steel block 20, is designed to act as a reverberant chamber, which means that the block 20 has many closely spaced mechanical resonances so that no predominant resonances exist and the sound field is uniform and diffused at all points within the block 20. In designing such a reverberant chamber, it is important to keep the block dimensions from being proportioned in even multiples, so as to prevent the normal modes of the block 20 from clustering around preferred frequencies. A rectangular block with dimensions proportioned as "one" to the "cube root of two" to the "cube root of four" has been found to give the desired performance. An example of a rectangular block 20 having such dimensions would be a block 20 being 10.0 × 7.95 × 6.30 inches. A steel block 20 constructed according to those dimensions will be satisfactory for the above-mentioned frequency range; namely, 100 kHz to 1.1 MHz. In addition to approximating the intended medium, the use of such a steel block 20 permits the standard transducer 12 and the acoustic emission transducer 18 to be mounted near each other while still receiving approximately the same acoustic signal level. Experimental data shows that the difference in sensitivity between any two locations on the block 20 is less than 1 dB. Also, the number of standing waves present is large enough to obtain valid results within the aforementioned range of frequencies.

Also connected to the steel block 20 is a means 22 for transmitting acoustic random, white noise into the block 20. Random white noise is used to approximate the background noise present during nuclear reactor operations, and provides a diffuse-field response. This may be, for example, an electronic random white noise generator 24 connected to a transmitting electroacoustic transducer 16 which, in turn, is acoustically coupled to the steel block 20. As used in this application, random white noise is defined as comprising oscillations which are statistically Gaussian in amplitude distribution, and which have a root mean square signal amplitude per unit bandwidth ratio which is constant as a function of frequency. Connected to the acoustic transducer 18 and the standard transducer 12 are a spectrum analyzer 26 and recording means 28 such as an X-Y recorder.

FIG. 3 is a flow diagram showing the flow of the electrical signals. The random acoustic white noise generator 24 transmits a signal into the bounded acoustical medium 20 and effectively excites all of the medium's resonances which lie within the frequency excitation band. The spectrum analyzer 26 is set to pass signals which are within a predetermined, selected bandwidth. For calibration of acoustic emission transducers 18 intended for use on nuclear reactors, a 10 kHz bandwidth details the nature of transducer resonances adequately. This 10 kHz bandwidth is wider than the bandwidth occupied by a large number of resonant standing waves within the steel block 20, while at the same time being narrower than the bandwidth of acoustic emission resonances, thereby rendering the calibration valid. Therefore, the spectrum analyzer can be set to allow signals to pass only within a 10 kHz bandwidth centered around a frequency which lies anywhere within the frequency range from 100 kHz to 1.1 MHz. The X-Y recorder 28 will record the magnitude of the spectrum analyzer outputs from both the acoustic emission transducer 18 and the standard receiving transducer 12 as a function of frequency, thereby obtaining graphic representations of the measured spectrums.

Figure 4:
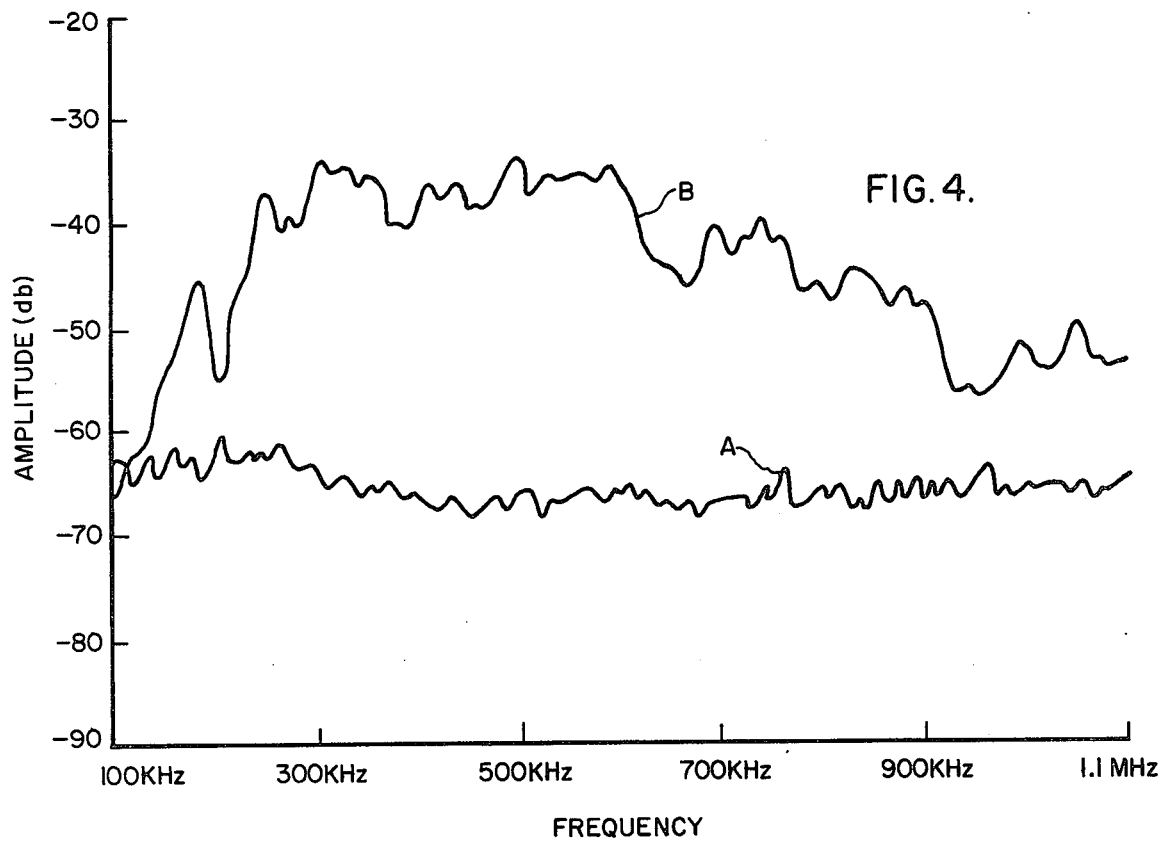
FIG. 4 illustrates typical output responses obtained during calibration.

The operation of the system is as follows. The bandwidth of the spectrum analyzer 26 is set equal to 10kHz. The switches 30, 32 close the circuit to the standard receiving transducer 12. The center frequency of the spectrum analyzer 26 is then continuously swept from 100 kHz to 1.1 MHz. The spectrum analyzer 26 allows only those responses within the predetermined 10 kHz bandwidth to pass through to the recorder 28, where the responses are registered in the vertical, or Y-axis. The spectrum analyzer 26 simultaneously transmits a voltage signal proportional to the value of the center frequency to the recorder 28, where the signal is registered on the horizontal, or X-axis. The recorder 28 thus plots the sound spectrum measured by the standard receiving transducer 12. The switches 30, 32 then close the circuit to the acoustic emission transducer 18, and the above-described measurement procedure is repeated, resulting in a graphic plot on the recorder 28 of the sound spectrum measured by the acoustic emission transducer 18. FIG. 4 illustrates a typical response curve for both the standard receiving transducer 12, designated by the letter A, and for the acoustic emission transducer 18, designated by the letter B.

The absolute magnitude of the output response of both the standard transducer 12 and the acoustic emission transducer 18, as shown in FIG. 4, is not utilized. This magnitude is within a range predetermined to give recordable outputs, and is dependent upon the output of the random noise generator 24. What is utilized is the relative difference between the two curves. The output response, A, of the standard transducer 12, is equated with the receiving sensitivity of the transducer 12 previously determined by the reciprocity calibration. By so equating, all points on curve A would be equal to the sensitivity $M_R$.

The receiving sensitivity of the acoustic emission transducer 18 is determined by first measuring the number of decibels by which its response curve B differs from the standard receiving transducer's response curve A at a specific frequency, and then adding or subtracting this decibel difference to the absolute sensitivity of the receiving transducer 12 at the same specific frequency. The receiving sensitivity of the receiving transducer 12, and of the acoustic emission transducer 18 is expressed in units of decibels referenced to 1 volt per microbar. (A microbar is a unit of pressure equal to 0.1 Newton/meter$^2$).

As an example, assume that the absolute receiving sensitivity of the standard transducer 12 as determined by the reciprocity calibration technique, was −124 dB, reference to 1 volt per microbar, throughout the frequency range of interest. Then, at 500 kHz, the response curve B of the acoustic emission transducer 18, as shown in FIG. 4, is 33 dB above the response curve A of the standard receiving transducer 12. This results in a receiving sensitivity for the acoustic emission transducer 18 of −91 dB referenced to 1 volt per microbar. (−124 dB + 33 dB = −91 dB). Similar comparisons are made at 10 kHz intervals, or other intervals if so desired, throughout the entire range of frequencies of interest to obtain a calibration of the receiving sensitivity of the acoustic emission transducer 18.

Thus, this invention provides a means for calibrating the receiving sensitivity of acoustic emission transducers to permit their utilization as passive monitoring devices to detect growing flaws in nuclear reactor pressure vessel walls.

I claim as my invention:

1. A method of calibrating an acoustic emission transducer to operate within a predetermined range of frequencies in a given application comprising:

determining the absolute receiving sensitivity of a standard transducer at selected frequencies within said range of frequencies;

placing said standard transducer and said acoustic emission transducer in acoustical communication with a surface of a bounded acoustic medium presenting a substantially equivalent acoustic loading to the medium on which the acoustic emission transducer is to be used in its given application, said bounded acoustic medium comprising a block, each dimension of said block being at least approximately equal to a thickness of said acoustic medium on which said acoustic emission transducer is to be used in its given application;

transmitting acoustic random white noise into said acoustic medium to establish a reverberant, diffuse sound field;

obtaining the output response of said primary transducer and said acoustic emission transducer to the reverberant, diffuse sound field at selected frequencies within said range of frequencies; and comparing said acoustic emission transducer output response with said standard transducer output response at said selected frequencies to determine the receiving sensitivity of said acoustic emission transducer.

2. A method according to claim 1 wherein comparing said acoustic emission transducer output response with said standard transducer output response comprises:

equating said standard transducer output response with said standard transducer sensitivity; and comparing said acoustic emission transducer output response with said standard transducer sensitivity.

3. The method according to claim 1 including utilizing a reciprocity calibration technique for determining the sensitivity of said standard transducer.

4. The method according to claim 1 including constructing said block of steel.

5. The method according to claim 1 including filtering said standard transducer output response and said acoustic emission transducer output response through a spectrum analyzer to obtain said responses within a predetermined bandwidth of frequencies at said selected frequencies.

6. The method according to claim 5 including transmitting said standard transducer output response and said acoustic emission transducer output response to a recorder.

7. A method of calibrating an acoustic emission transducer to operate within a predetermined range of frequencies in a given application comprising:

determining the absolute receiving sensitivity of a standard transducer at selected frequencies within said range of frequencies;

placing said standard transducer and said acoustic emission transducer in acoustical communication with a surface of a bounded acoustic medium presenting a substantially equivalent acoustic loading to the medium on which the acoustic emission transducer is to be used in its given application, said bounded acoustic medium comprising a rectangular block dimensioned according to the proportion one to the cube root of two to the cube root of four;

transmitting acoustic random white noise into said acoustic medium to establish a reverberant, diffuse sound field;

obtaining the output response of said primary transducer and said acoustic emission transducer to the reverberant, diffuse sound field at selected frequencies within said range of frequencies; and comparing said acoustic emission transducer output response with said standard transducer output response at said selected frequencies to determine the receiving sensitivity of said acoustic emission transducer.

* * * * *